US009625470B2

(12) United States Patent
Coon et al.

(10) Patent No.: US 9,625,470 B2
(45) Date of Patent: Apr. 18, 2017

(54) IDENTIFICATION OF RELATED PEPTIDES FOR MASS SPECTROMETRY PROCESSING

(71) Applicant: Wisconsin Alumni Research Foundation, Madison, WI (US)

(72) Inventors: Joshua Jacques Coon, Middleton, WI (US); Michael Scott Westphall, Fitchburg, WI (US); Derek James Bailey, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 874 days.

(21) Appl. No.: 13/888,841

(22) Filed: May 7, 2013

(65) Prior Publication Data

US 2014/0336951 A1   Nov. 13, 2014

(51) Int. Cl.
*G06F 19/00* (2011.01)
*G01N 33/68* (2006.01)
*H01J 49/00* (2006.01)

(52) U.S. Cl.
CPC ...... *G01N 33/6848* (2013.01); *H01J 49/0031* (2013.01); *H01J 49/0036* (2013.01)

(58) Field of Classification Search
CPC ........... A61K 9/14; A61K 9/145; A61K 9/146
USPC .................... 702/23, 24, 182–185
See application file for complete search history.

(56) References Cited

U.S. PATENT DOCUMENTS 8,227,251 B2   7/2012 Ranish et al.

2005/0288865 A1* 12/2005 Appel et al. ............... 702/19
2011/0288779 A1   11/2011 Satulovsky
2012/0261568 A1   10/2012 Coon et al.

FOREIGN PATENT DOCUMENTS

EP   1916526   4/2008

OTHER PUBLICATIONS

Dauly et al., In-Depth, Comprehensive Mapping of the Human Seminal Plasma Proteome by a Novel, Iterative LC-MS/MS Analysis and Database Search Workflow, Thermo Scientific , 2009, pp. 1-8.
Robinson et al., Enhanced Sample Multiplexing for Nitrotyrosine-Modified Proteins Using Combined Precursor Isotopic Labeling and Isobaric Tagging, Analytical Chemistry, vol. 84, Apr. 17, 2012, pp. 4677-4686.
Yan et al., Index-ion Triggered MS2 Ion Quantification: A Novel Proteomics Approach for Reproducible Detection and Quantification of Targeted Proteins in Complex Mixtures, Molecular & Cellular Proteomics, vol. 10, Dec. 17, 2010, pp. 1-15.

(Continued)

*Primary Examiner* — Edward Raymond
(74) *Attorney, Agent, or Firm* — Bell & Manning, LLC

(57) ABSTRACT

A method of identifying a related peak set from MS1 spectra data is provided. An intensity peak is selected from MS1 spectra data generated for a sample by a tandem mass spectrometer. A peak location is identified for the selected intensity peak. An intensity score is calculated from the MS1 spectra data for each of a plurality of possible related peak locations based on an intensity value associated with each of the plurality of possible related peak locations. Whether or not any of the plurality of possible related peak locations forms a related peak set is determined based on the calculated intensity score for each of the plurality of possible related peak locations.

20 Claims, 12 Drawing Sheets

(56) References Cited

OTHER PUBLICATIONS

Zhang et al., Automated Comparative Proteomics Based on Multiplex Tandem Mass Spectrometry and Stable Isotope Labeling, Molecular & Cellular Proteomics, vol. 5, Oct. 27, 2005, pp. 401-411.
Yan et al., Mass spectrometry-based quantitative proteomic profiling, Briefings in Functional Genomics and Proteomics, vol. 4, No. 1, May 2005, pp. 27-38.
Escher et al., Using iRT, a normalized retention time for more targeted measurement of peptides, Proteomics, vol. 12, No. 8, May 11, 2012, pp. 1111-1121.
Gallien et al., Highly multiplexed targeted proteomics using precise control of peptide retention time, Proteomics, vol. 12, No. 8, May 11, 2012, pp. 1122-1133.
Zhang et al., Review of Peak Detection Algorithms in Liquid-Chromatography-Mass Spectrometry, Current Genomics, vol. 10, No. 6, 2009, pp. 388-401.
Kristjansdottir et al., Strategies and Challenges in Measuring Protein Abundance Using Stable Isotope Labeling and Tandem Mass Spectrometry. Tandem Mass Spectrometry—Applications and Principles, Dr. Jeevan Prasain (Ed.), InTech, Feb. 29, 2012, pp. 235-258.
Titulaer et al., Label-free peptide profiling of Orbitrap™ full mass spectra, BMC Research Notes, vol. 4, No. 21, Jan. 27, 2011, pp. 1-17.
Carvalho et al., XDIA: improving on the label-free data-independent analysis, BIOINFORMATICS, vol. 26, No. 6, Jan. 26, 2010, pp. 847-848.
Pisitkun et al., Tandem Mass Spectrometry in Physiology, PHYSIOLOGY, vol. 22, Dec. 2007, pp. 390-400.

\* cited by examiner

| Tags | Selected Peak | Score |
|---|---|---|
| 1 | Light | 7.3 |
| 2 | Light | 7.3 |
| 3 | Light | 7.3 |
| 4 | Light | 7.3 |
| 5 | Light | 7.3 |
| 1 | Medium | 7.3 |
| 2 | Medium | 14.5 |
| 3 | Medium | 7.3 |
| 4 | Medium | 14.5 |
| 5 | Medium | 7.3 |
| 1 | Heavy | 14.5 |
| 2 | Heavy | 21.8 |
| 3 | Heavy | 7.3 |
| 4 | Heavy | 14.5 |
| 5 | Heavy | 7.3 |

Fig. 8

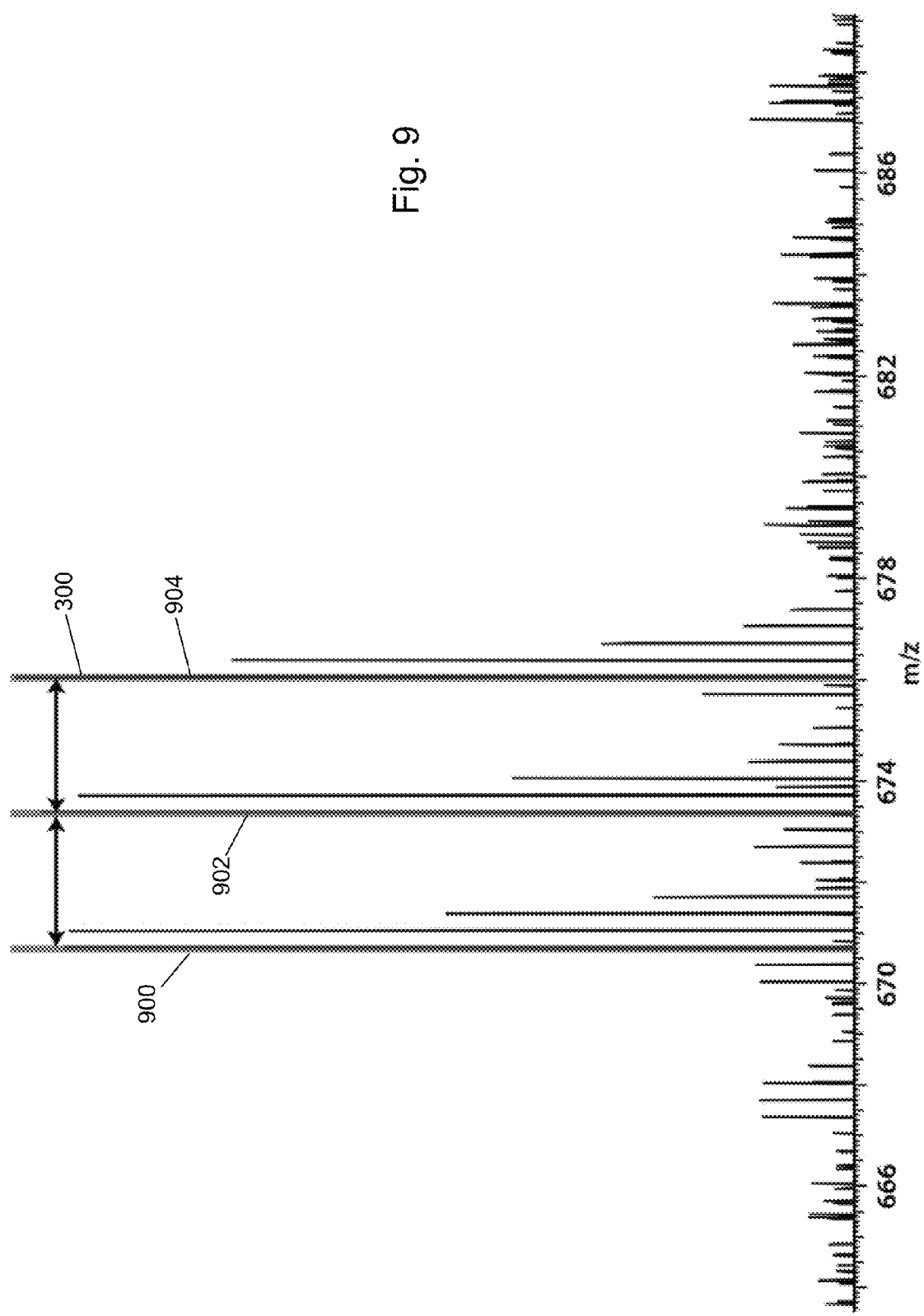

IDENTIFICATION OF RELATED PEPTIDES FOR MASS SPECTROMETRY PROCESSING

REFERENCE TO GOVERNMENT RIGHTS

This invention was made with government support under R01GM080148 awarded by the National Institutes of Health. The government has certain rights in the invention.

BACKGROUND

The identification and quantification of proteins in complex biological samples is critically important to biological and biomedical research. Tandem mass spectrometry (MS/MS) is a technique capable of identifying large numbers of proteins in complex biological samples. In a typical experiment, proteins are digested with site-specific reagents to produce smaller peptides, the peptides are separated via high-performance liquid chromatography (HPLC) and the separated peptides are injected onto a tandem mass spectrometer. In such an experiment, as the peptides elute from the liquid chromatography (LC) column, they are subjected to an ionizing voltage and are introduced into the near vacuum environment of the tandem mass spectrometer. A survey scan (i.e., a first mass spectrum or MS1) is obtained to determine the mass-to-charge ratio (m/z) of the intact peptides that entered the tandem mass spectrometer. The ionized peptides detected in the first mass spectrum may be referred to as precursor ions. One or more of the precursor ions in the first mass spectrum is selected, sequentially isolated, fragmented and the resulting fragment ion m/z values determined in a second mass spectrum (i.e., MS/MS or MS2). Generally, only the most intense precursor ions are selected for generation of the second mass spectrum. The fragment ions detected in the second mass spectrum may be referred to as product ions. This process is repeated to automatically acquire MS/MS spectra of as many of the precursor ions as possible. The charge state and peptide mass are obtained from the first mass spectrum while the fragmentation pattern is recorded in the second mass spectrum. With this information it is possible to identify the peptide and protein of origin, e.g., by comparison to peptide fragmentation patterns stored in a database. The procedure is repeated time and time again, as quickly as possible, to sample as many peptides in the sample as possible.

As described above, tandem mass spectrometry permits the identification of peptides and proteins. However, it is also important to quantify peptides and proteins, e.g., to compare the amount of a particular protein among two or more different samples (e.g., replicate samples, samples subject to different experimental conditions, samples from different time points, samples from different laboratory animals, etc.). One approach for quantitative proteomics involves combining tandem mass spectrometry with stable isotope labeling techniques. Depending upon the type of stable isotope labeling technique, quantification can be obtained from MS1 spectra or MS2 spectra or both.

As an example of a stable isotope labeling technique that can provide quantification from MS1 spectra, one sample (e.g., a sample containing peptides) is left with its natural isotope abundance (unlabeled) and the other sample is made to incorporate a heavy isotope (labeled). The two samples are mixed and analyzed simultaneously (i.e., by injection into the HPLC and tandem mass spectrometer). A labeled peptide and its unlabeled counterpart have the same chemical formula and same chemical structure and thus, will elute together from the LC column. However, the introduction of the isotope label results in a predictable mass difference between such peptides, resulting in the appearance of "peptide pairs" in the MS1 spectra. By comparing the signal intensities of the labeled and unlabeled peptide pairs, relative quantification is obtained. Absolute quantification may be obtained if the labeled sample is replaced with synthetic peptides of known quantity. In either case, the quantitative values are obtained from the MS1 spectra. Techniques for stable isotope labeling and quantification from MS1 spectra include, for example, stable isotope labeling with amino acids in cell culture (SILAC). In a "two-plex" SILAC experiment, two different samples are compared simultaneously by using light (e.g., unlabeled) and heavy labeled peptides. In a "three-plex" SILAC experiment, three different samples are compared simultaneously by using light (e.g., unlabeled), medium and heavy labeled peptides.

As an example of a stable isotope labeling technique that can provide quantification from MS2 spectra, samples (e.g., samples containing peptides) are labeled with a set of isobaric tags. The samples, each labeled with a different isobaric tag from the set, are mixed and analyzed simultaneously. The isobaric tags in the set have the same chemical formula and same chemical structure and thus, the different versions of a labeled peptide (e.g., a peptide labeled with one of the isobaric tags from the set and the same peptide labeled with another of the isobaric tags) will elute together from the LC column. The isobaric tags also have the same mass and thus, the different versions of the labeled peptide will be indistinguishable in the MS1 spectra. However, upon fragmentation and separation in the MS2 spectra, each isobaric tag in the set releases a reporter ion having a different mass. By comparing the signal intensities of the reporter ions, relative quantification is obtained. Thus, the quantitative values are obtained from the MS2 spectra. Techniques for stable isotopic labeling and quantification from MS2 spectra include, for example, tandem mass tags (TMT) and isobaric tags for relative and absolute quantitation (iTRAQ). In a "six-plex" TMT experiment, six different samples may be compared simultaneously using a set of six isobaric tags. In an "eight-plex" iTRAQ experiment, eight different samples may be compared simultaneously using a set of eight isobaric tags.

In order to further increase the multiplexing capabilities of quantitative proteomics, i.e., the ability to analyze an even greater number of samples simultaneously, the stable isotopic labeling techniques involving quantification from MS1 spectra may be combined with techniques involving quantification from MS2 spectra. As one example, bio-duplicate samples could be distinguished in the MS1 spectra through the use of a light (e.g., unlabeled) and heavy isotopic label and each replicate could be analyzed at six time points with each time point distinguished in the MS2 spectra by a different six-plex isobaric tag, allowing the multiplex analysis of 12 samples at one time.

However, the potential of such multiplex experiments has been limited. As noted above, tandem mass spectrometer systems typically select only the most intense precursor ions for generation of the second mass spectrum. If a group of peaks (e.g., two peaks) as distinguished in the MS1 spectra and corresponding to an isotopically labeled peptide are not among the most intense peaks in the MS1 spectra, it is possible that not all peaks in the group will be selected for generation of MS2 spectra, precluding a quantitative comparison among the different samples. Moreover, even if all peaks in the group are selected, tandem mass spectrometer systems typically do not coordinate the timing of the MS2 spectra generated for the peaks. If significant time intervals separate the MS2 spectra generated for each peak in the group, the changing chemical background in the system may degrade the quantitative accuracy.

SUMMARY

In an illustrative embodiment, a method is provided for identifying a related peak set from MS1 spectra data. An intensity peak is selected from the MS1 spectra data generated for a sample by a tandem mass spectrometer. A peak location is identified for the selected intensity peak. An intensity score is calculated from the MS1 spectra data for each of a plurality of possible related peak locations based on an intensity value associated with each of the plurality of possible related peak locations. Whether or not any of the plurality of possible related peak locations forms a related peak set is determined based on the calculated intensity score for each of the plurality of possible related peak locations.

In another illustrative embodiment, a computer-readable medium is provided having stored thereon computer-readable instructions that when executed by a computing device, cause the computing device to perform the method for identifying a related peak set from MS1 spectra data.

In yet another illustrative embodiment, a device is provided. The device includes, but is not limited to, a processor and a computer-readable medium operably coupled to the processor. The computer-readable medium has instructions stored thereon that, when executed by the processor, cause the device to perform the method for identifying a related peak set from MS1 spectra data.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 8 depicts a table of intensity based scores calculated for a plurality of sets of triplex data points in accordance with an illustrative embodiment.

FIG. 9 depicts the zoomed MS1 mass spectrum plot of FIG. 4 including a fourth set of triplex data points selected as a matching triplex for MS2 mass spectrum analysis in accordance with an illustrative embodiment.

DETAILED DESCRIPTION

Figure 1:
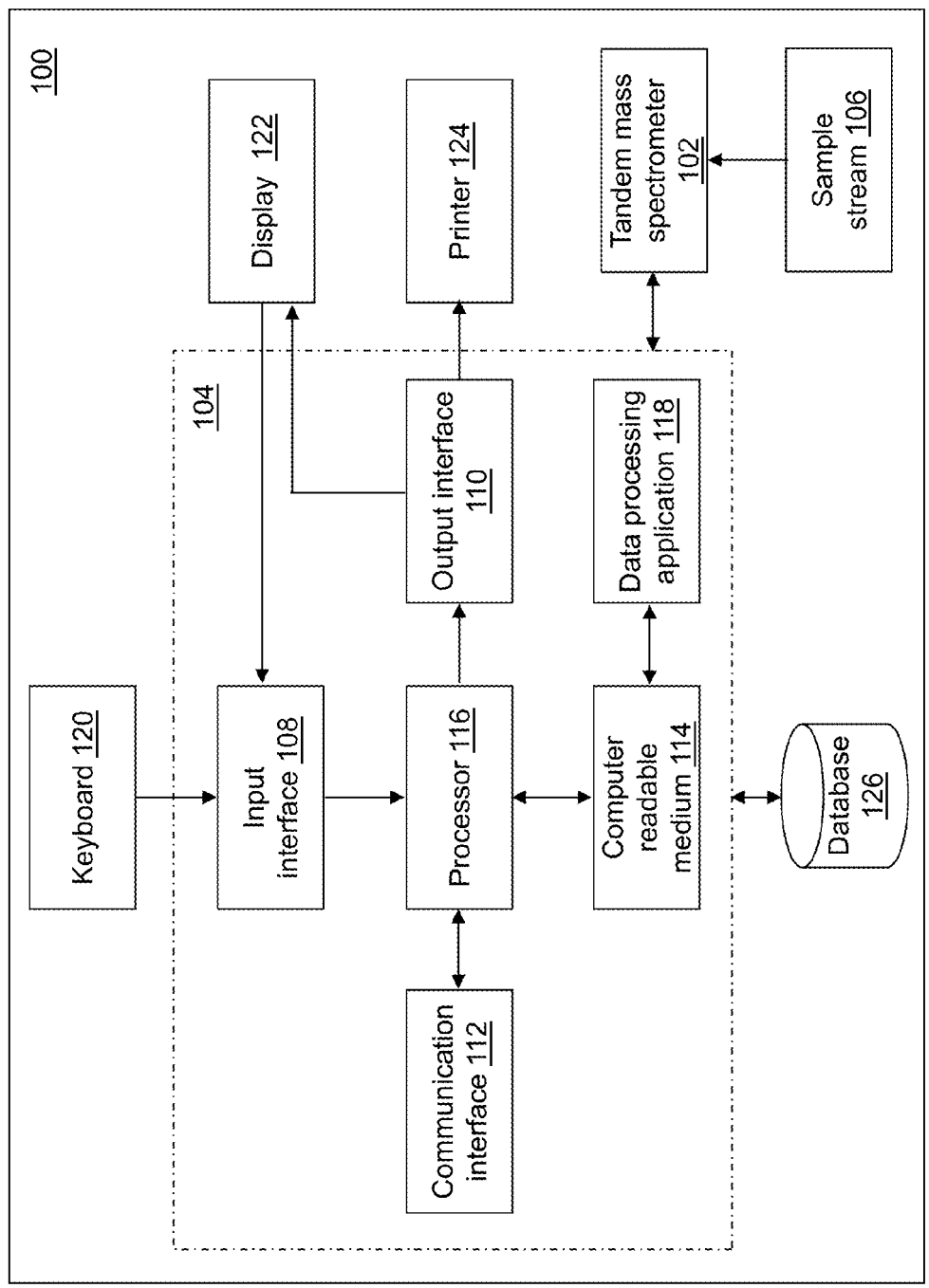
FIG. 1 depicts a block diagram of a tandem mass spectrometer data processing system in accordance with an illustrative embodiment.

With reference to FIG. 1, a block diagram of a tandem mass spectrometer data processing system 100 is shown in accordance with an illustrative embodiment. Tandem mass spectrometer data processing system 100 may include a tandem mass spectrometer 102, a computing device 104, and a database 126. Fewer, different, and additional components may be incorporated into tandem mass spectrometer data processing system 100.

Tandem mass spectrometer 102 is configured to perform two or more stages of mass spectrometry and includes an ion source, one or more mass analyzers, and a detector (not shown). The ion source operates to produce precursor ions from analytes present in a sample stream 106. The ion source may be implemented in a variety of ways, such as, but not limited to, using electrospray ionization (ESI). The mass analyzers receive ions (e.g., from the ion source or a collision cell as discussed below) and may operate to separate and/or to select ions by their mass-to-charge ratios (m/z). The mass analyzers may be implemented in a variety of ways, such as, but not limited to using ion trap, time-of-flight, quadrupole, Orbitrap, and Fourier transform ion cyclotron analyzers. Tandem mass spectrometer 102 may be configured to perform tandem mass spectrometry in time or in space depending upon the choice of mass analyzer(s). The detector receives ions (i.e., from a mass analyzer) and operates to count the number of ions at a particular m/z value. The detector may be implemented in a variety of ways, such as, but not limited to, using an electron multiplier or a scintillation counter. Tandem mass spectrometer 102 may optionally include a collision cell positioned between two mass analyzers which can operate to induce fragmentation of precursor ions to produce product ions. The collision cell may be implemented in a variety of ways, such as, but not limited to, using collision-induced dissociation (CID). In an illustrative embodiment, tandem mass spectrometer 102 is a Thermo Scientific Orbitrap Elite hybrid mass spectrometer. Tandem mass spectrometers of different types, resolution, manufacture, and model may be used in alternative embodiments without limitation.

Sample stream 106 may include analytes dispersed in a solvent. Analytes include a variety of biomolecules such as, but not limited to, proteins and peptides. Other analytes, such as pharmaceutical compounds, may be used. The analytes may be derived from a variety of samples, such as, but not limited to, those of viral, prokaryote, bacterial, eukaryote, fungal, yeast, vegetal, invertebrate, vertebrate, mammalian, or human origin. The samples may be processed to provide, for example, extracted protein fractions or digested proteins. The samples may be further processed to provide, for example, proteins or peptides that have been tagged or labeled using a stable isotopic labeling technique for providing quantification from MS1 spectra or MS2 spectra or both. Sample stream 106 may be introduced into tandem mass spectrometer 102 in a continuous fashion from a fractionation system such as a high-performance liquid chromatography (HPLC) system, whereby successive eluting portions of the sample stream 106 are analyzed by tandem mass spectrometer data processing system 100. Other fractionation systems may be used, such as, but not limited to, gas chromatography systems, affinity chromatography systems, and capillary electrophoresis systems.

Database 126 is a data repository for tandem mass spectrometer data processing system 100. Database 126 may include a plurality of databases that may be organized into multiple database tiers to improve data management and access. Database 126 may utilize one or more database technologies as known to those skilled in the art including a file system, a relational database, a system of tables, a structured query language database, etc. Database 126 may be implemented as a single database or as multiple databases stored in different storage locations distributed over the Internet or in other storage infrastructures.

Computing device 104 may include an input interface 108, an output interface 110, a communication interface 112, a computer-readable medium 114, a processor 116, and a data processing application 118. Computing device 104 may be a computer of any form factor including an electrical circuit board integrated into tandem mass spectrometer 102. Different, fewer, and additional components may be incorporated into or integrated with computing device 104.

Input interface 108 provides an interface for receiving information into computing device 104 as understood by those skilled in the art. Input interface 110 may interface with various input technologies including, but not limited to, a keyboard 120, a display 122, a mouse, a track ball, a keypad, one or more buttons, etc. to allow the user to enter information into computing device 104 or to make selections presented in a user interface displayed on display 122. Display 122 may be a thin film transistor display, a light emitting diode display, a liquid crystal display, or any of a variety of different displays known to those skilled in the art. Input interface further may provide the electrical connections that provide connectivity between computing device 104 and tandem mass spectrometer 102 and/or between computing device 104 and database 126. Computing device 104 may have one or more input interfaces that use the same or a different interface technology. Display 122, keyboard 120, etc. further may be accessible by computing device 104 through communication interface 112.

Output interface 110 provides an interface for outputting information from computing device 104. For example, output interface 110 may interface with various output technologies including, but not limited to, display 122, a printer 124, etc. Printer 124 may be any of a variety of printers as known to those skilled in the art. Computing device 104 may have one or more output interfaces that use the same or a different interface technology. Printer 124 and other output technologies further may be accessible by computing device 104 through communication interface 112.

Communication interface 112 provides an interface for receiving and transmitting data between devices using various protocols, transmission technologies, and media as known to those skilled in the art. Communication interface 112 may support communication using various transmission media that may be wired or wireless. Computing device 104 may have one or more communication interfaces that use the same or a different communication interface technology. Data and messages may be transferred between computing device 104 and tandem mass spectrometer 102 and/or database 126 using communication interface 112.

Computer-readable medium 114 is an electronic holding place or storage for information so that the information can be accessed by processor 116 as understood by those skilled in the art. Computer-readable medium 114 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., compact disc (CD), digital versatile disc (DVD), . . . ), smart cards, flash memory devices, etc. Computing device 104 may have one or more computer-readable media that use the same or a different memory media technology. Computing device 104 also may have one or more drives that support the loading of a memory media such as a CD or DVD.

Processor 116 executes instructions as known to those skilled in the art. The instructions may be carried out by a special purpose computer, logic circuits, or hardware circuits. Thus, processor 116 may be implemented in hardware, firmware, or any combination of these methods and/or in combination with software. The term "execution" is the process of running an application or the carrying out of the operation called for by an instruction. The instructions may be written using one or more programming language, scripting language, assembly language, etc. Processor 116 executes an instruction, meaning that it performs/controls the operations called for by that instruction. Processor 116 operably couples with input interface 108, with output interface 110, with computer-readable medium 114, and with communication interface 112 to receive, to send, and to process information. Processor 116 may retrieve a set of instructions from a permanent memory device and copy the instructions in an executable form to a temporary memory device that is generally some form of RAM. Computing device 104 may include a plurality of processors that use the same or a different processing technology.

Data processing application 118 performs operations associated with processing tandem mass spectrometer data to sample partner peaks associated with related analytes, e.g., related peptides, in succession. Some or all of the operations described herein may be embodied in data processing application 118. The operations may be implemented using hardware, firmware, software, or any combination of these methods. With reference to the example embodiment of FIG. 1, data processing application 118 is implemented in software (comprised of computer-readable and/or computer-executable instructions) stored in computer-readable medium 114 and accessible by processor 116 for execution of the instructions that embody the operations of data processing application 118. Data processing application 118 may be written using one or more programming languages, assembly languages, scripting languages, etc.

Tandem mass spectrometer 102, computing device 104, and database 126 may be integrated into a single device or their functionality may be distributed across one or more devices that are connected directly or through a network that may be wired and/or wireless. For example, tandem mass spectrometer 102 may connect to computing device 104 using a cable for transmitting information between tandem mass spectrometer 102 and computing device 104. As another example, tandem mass spectrometer 102, computing device 104, and/or database 126 may be remote from one another.

Figure 2:
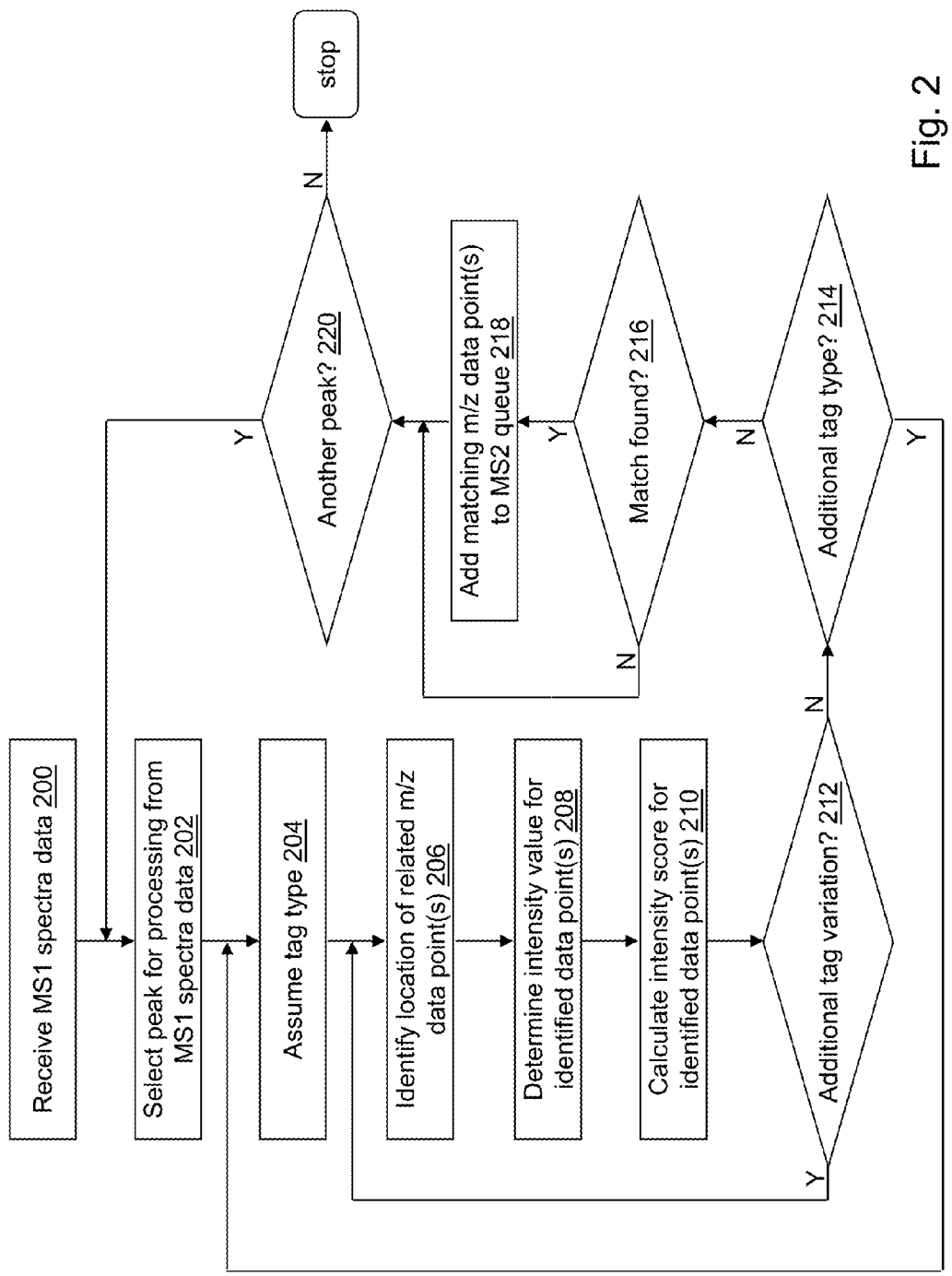
FIG. 2 depicts a flow diagram illustrating example operations performed by a data processing application of the tandem mass spectrometer data processing system of FIG. 1 in accordance with an illustrative embodiment.

With reference to FIG. 2, exemplary operations associated with data processing application 118 are described. Additional, fewer, or different operations may be performed depending on the embodiment. The order of presentation of the operations of FIG. 2 is not intended to be limiting. Thus, although some of the operational flows are presented in sequence, the various operations may be performed in various repetitions, concurrently, and/or in other orders than those that are illustrated.

In an operation 200, MS1 spectra data are received from tandem mass spectrometer 102 for processing by processor 116. The MS1 spectra data may be stored to computer-readable medium 114 or database 126 after receipt by computing device 104 from tandem mass spectrometer 102 and received in operation 200 by reading from computer-readable medium 114 or database 126. The MS1 spectra data further may be received in operation 200 by being streamed to computing device 104 from tandem mass spectrometer 102 through communication interface 112 or input interface 108. The MS1 spectra data includes data describing a relationship between the mass of a given ion and the number of elementary charges that it carries, which may be referred to as a mass-to-charge ratio (m/z). A signal intensity of the ions is associated with the mass-to-charge ratio. When using counting detectors the intensity is often measured in counts per second (cps). When using analog detection electronics the intensity is typically measured in volts. In some mass spectrometers, the intensity is related to the power (~amplitude squared) of the signal sine wave, which may be reduced to a root-mean-square power as understood by a person of skill in the art. In most forms of mass spectrometry, the intensity of ion current measured by the spectrometer does not accurately represent relative abundance, but correlates loosely with it. Thus, the y-axis generally may be labeled as indicating the relative abundance of the ion.

Figure 3:
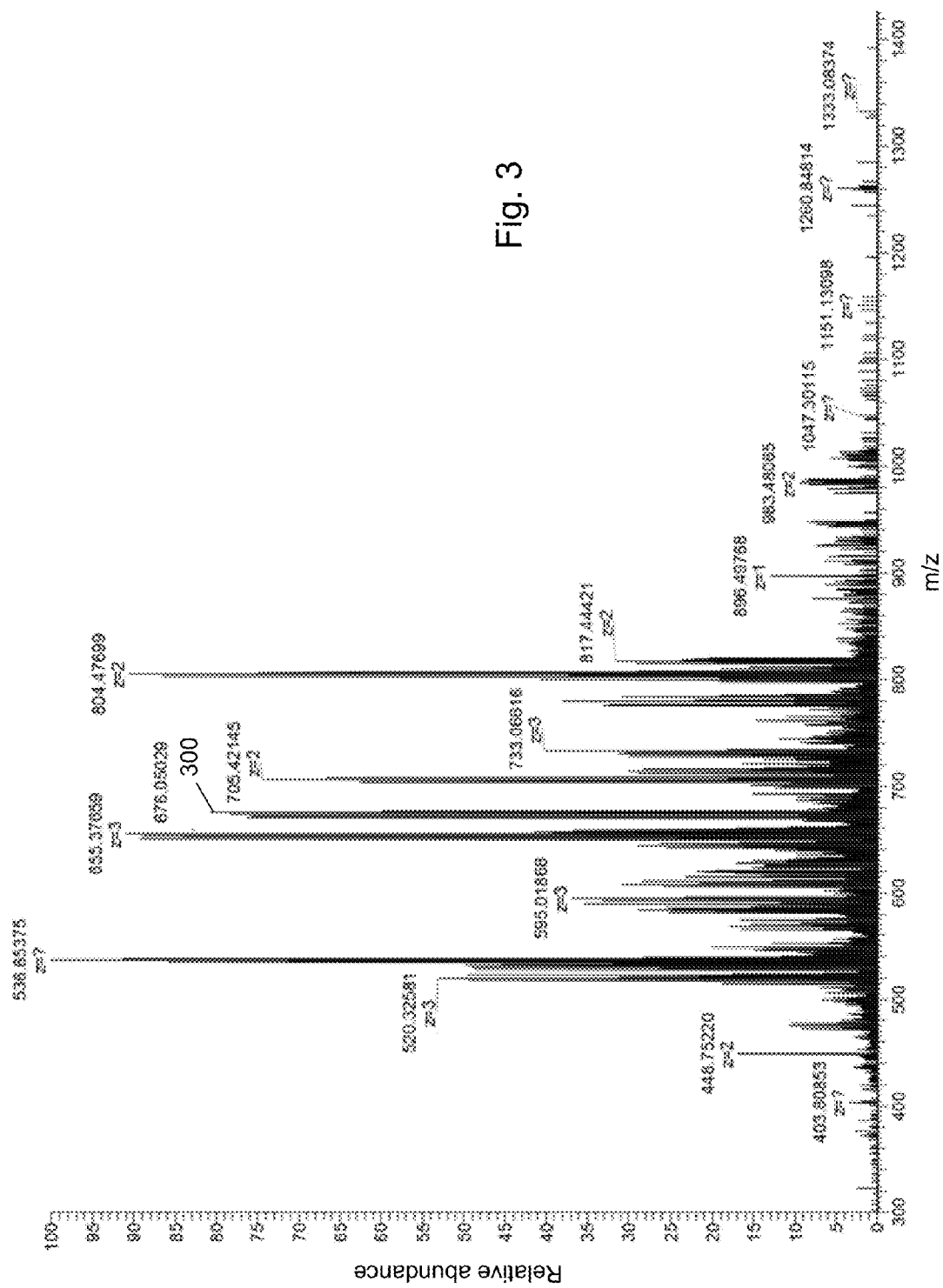
FIG. 3 depicts an MS1 mass spectrum plot of an isochemic peptide elution profile at a selected point in time in accordance with an illustrative embodiment.
Figure 4:
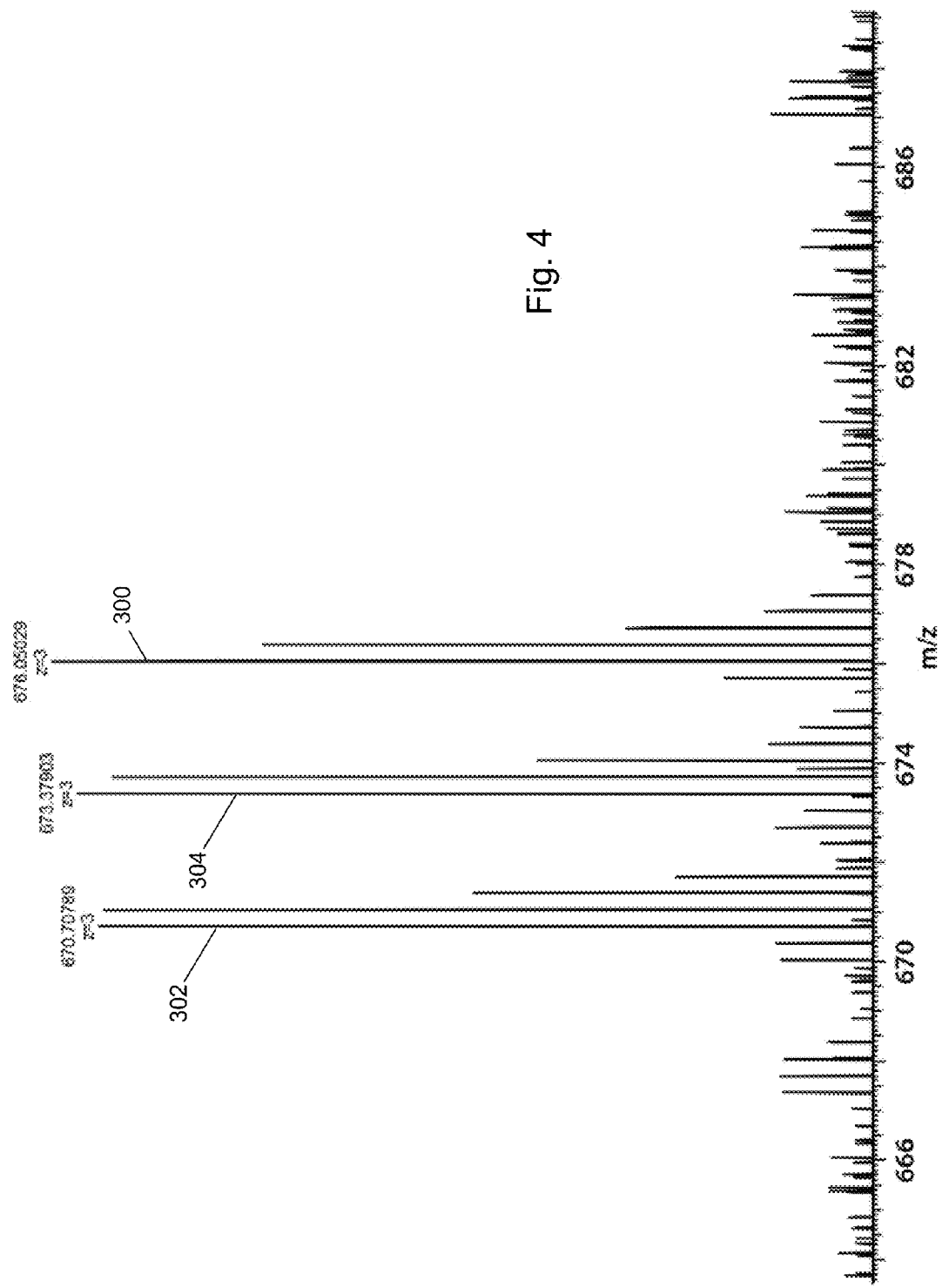
FIG. 4 depicts the MS1 mass spectrum plot of FIG. 3 zoomed to show a specific m/z range of interest.

For example, with reference to FIG. 3, an MS1 mass spectrum plot of an isochemic peptide elution profile at a selected point in time is shown in accordance with an illustrative embodiment. With reference to FIG. 4, the MS1 mass spectrum plot of FIG. 3 is zoomed to show a specific m/z range of interest.

In an operation 202, intensity peaks are identified in the received MS1 spectra data. As part of defining an experiment, a user may define a number of the highest intensity peaks that are to be selected for MS2 analysis. For example, the intensity peaks may be identified using the top N most intense peaks from a mass spectrum that are not currently being excluded (i.e. dynamic exclusion) where N≈10 in an illustrative embodiment. As an illustrative alternative, the lowest intensity peaks exceeding a noise threshold may be selected for MS2 analysis. For illustration, with reference to FIGS. 3 and 4, a first peak 300 is selected from the MS1 spectra data. In the illustrative embodiment, a second peak 302, a third peak 304, and first peak 300 are related peaks associated with a light, a medium, and a heavy tag type, respectively. Though these peaks are visually identifiable, the set of related peak locations is not known a priori.

With continuing reference to FIG. 2, in an operation 204, the selected intensity peak is assumed to be associated with an initial tag type. For example, various tagging or labeling methods may be used that result in a set of related peaks in the MS1 mass spectrum plot. An example tag type of the set of related peaks may be the light peptide version in a group of related peptides that may include a light peptide version, a medium peptide version, and a heavy peptide version. Of course, different numbers of related peptides may be defined depending on the tagging/labeling method used. The tagging/labeling methods are not particularly limited and can include various stable isotopic labeling techniques such as isobaric tagging, SILAC labeling, etc. The phrase "tag type" is meant to include peptides that may have been labeled with separate molecules as in isobaric tagging, as well as peptides that may have been labeled by incorporating isotopically labeled amino acids as in SILAC.

Additionally, a peptide in a set of related peaks may have a range of possible numbers of tags. Further, in some cases, a charge state is known for a peptide in a set of related peaks, while in others, a charge state of the peptide is not known and may also exhibit a range of possible values. As a result, a range of values for each may be defined and searched. As part of defining an experiment, a user may define a number of tag types indicating the number of possible peptide versions (light, medium1, medium2, heavy, etc.). The number of tag types defines the number of peaks in a set of related peaks. For example, if the possible peptide versions are light, medium1, medium2, and heavy, a set of related peaks includes four peaks with one peak associated with each peptide version. The user further may define a tag number indicating the number of possible tags for each peak in the set of related peaks and/or a charge state number indicating the number of possible charge states to be analyzed for each peak in the set of related peaks selected in operation 202. The tag type is an unknown associated with the selected peak, whereas the number of tags and possible charge states may be unknowns relative to identifying the related peaks in the set of related peaks to the selected peak. For illustration, the selected peak may be assumed to be the light peptide version in operation 204. On a subsequent execution of operation 204, the selected peak may be assumed to be the medium1 peptide version, and so on. Of course, the selection order may vary and may be definable by the user as an input.

In an operation 206, a location of the related peaks in the set of related peaks defined by the number of tag types is identified relative to the selected intensity peak based on the assumed number of tags and/or charge state number. For example, a location of one or more additional peak locations may be determined by calculating a differential location value as $$\Delta m/z = \frac{N_T \times m}{N_C}$$

where $N_T$ is the number of tags, m is the mass defined based on the chemical tag type, and $N_C$ is the charge state number assumed for this iteration in operation 204. Of course, in some experiments, $N_C$ may be known and thus, there is no need to iterate over values of the possible charge states.

Because the tag type was initially assumed to be the lightest of the related peaks, the calculated $\Delta m/z$ is successively applied to determine a possible location of each additional related peak in the set of related peaks. For example, if there are light and heavy peptide tag types in the experiment, only one related peak is assumed to possibly be at a first m/z value of $(m/z)_{SP}+\Delta m/z$, where $(m/z)_{SP}$ is the m/z location of the selected peak. If there are light, medium, and heavy peptide tag types in the experiment, two related peaks are assumed to possibly be at a first m/z value of $(m/z)_{SP}+\Delta m/z$ and at a second m/z value of $(m/z)_{SP}+2\times\Delta m/z$. If there are light, medium1, medium2, and heavy peptide tag types in the experiment, three related peaks are assumed to possibly be at a first m/z value of $(m/z)_{SP}+\Delta m/z$, at a second m/z value of $(m/z)_{SP}+2\times\Delta m/z$, and at a third m/z value of $(m/z)_{SP}+3\times\Delta m/z$. Of course, there may be additional tag types as understood by a person of skill in the art.

If the tag type was assumed to be the heaviest of the related peaks, the calculated $\Delta m/z$ is successively applied by subtracting the calculated Δm/z to determine a possible location of each additional related peak. For example, if there are light and heavy peptide tag types in the experiment, only one related peak is assumed to possibly be at a first m/z value of $(m/z)_{SP}-\Delta m/z$. If there are light, medium, and heavy peptide tag types in the experiment, two related peaks are assumed to possibly be at a first m/z value of $(m/z)_{SP}-\Delta m/z$ and at a second m/z value of $(m/z)_{SP}-2\times\Delta m/z$. If there are light, medium1, medium2, and heavy peptide tag types in the experiment, three related peaks are assumed to possibly be at a first m/z value of $(m/z)_{SP}-\Delta m/z$, at a second m/z value of $(m/z)_{SP}+2\times\Delta m/z$, and at a third m/z value of $(m/z)_{SP}+3\times\Delta m/z$. Of course, there may be additional tag types as understood by a person of skill in the art.

Of course, if the tag type was assumed to be an intermediate peak of the related peaks, the calculated Δm/z is successively applied by a combination of adding and subtracting the calculated Δm/z to determine a possible location of each additional related peak of the set of related peaks. For example, if there are light, medium, and heavy peptide tag types in the experiment, two related peaks are assumed to possibly be at a first m/z value of $(m/z)_{SP}-\Delta m/z$ and at a second m/z value of $(m/z)_{SP}+\Delta m/z$. If there are light, medium1, medium2, and heavy peptide tag types in the experiment, and the selected peak is assumed to be the medium1 tag type, three related peaks are assumed to possibly be at a first m/z value of $(m/z)_{SP}-\Delta m/z$, at a second m/z value of $(m/z)_{SP}+\Delta m/z$, and at a third m/z value of $(m/z)_{SP}+2\times\Delta m/z$. If there are light, medium1, medium2, and heavy peptide tag types in the experiment, and the selected peak is assumed to be the medium2 tag type, three related peaks are assumed to possibly be at a first m/z value of $(m/z)_{SP}-2\times\Delta m/z$, at a second m/z value of $(m/z)_{SP}-\Delta m/z$, and at a third m/z value of $(m/z)_{SP}+\Delta m/z$. Of course, there may be additional tag types as understood by a person of skill in the art.

Figure 5:
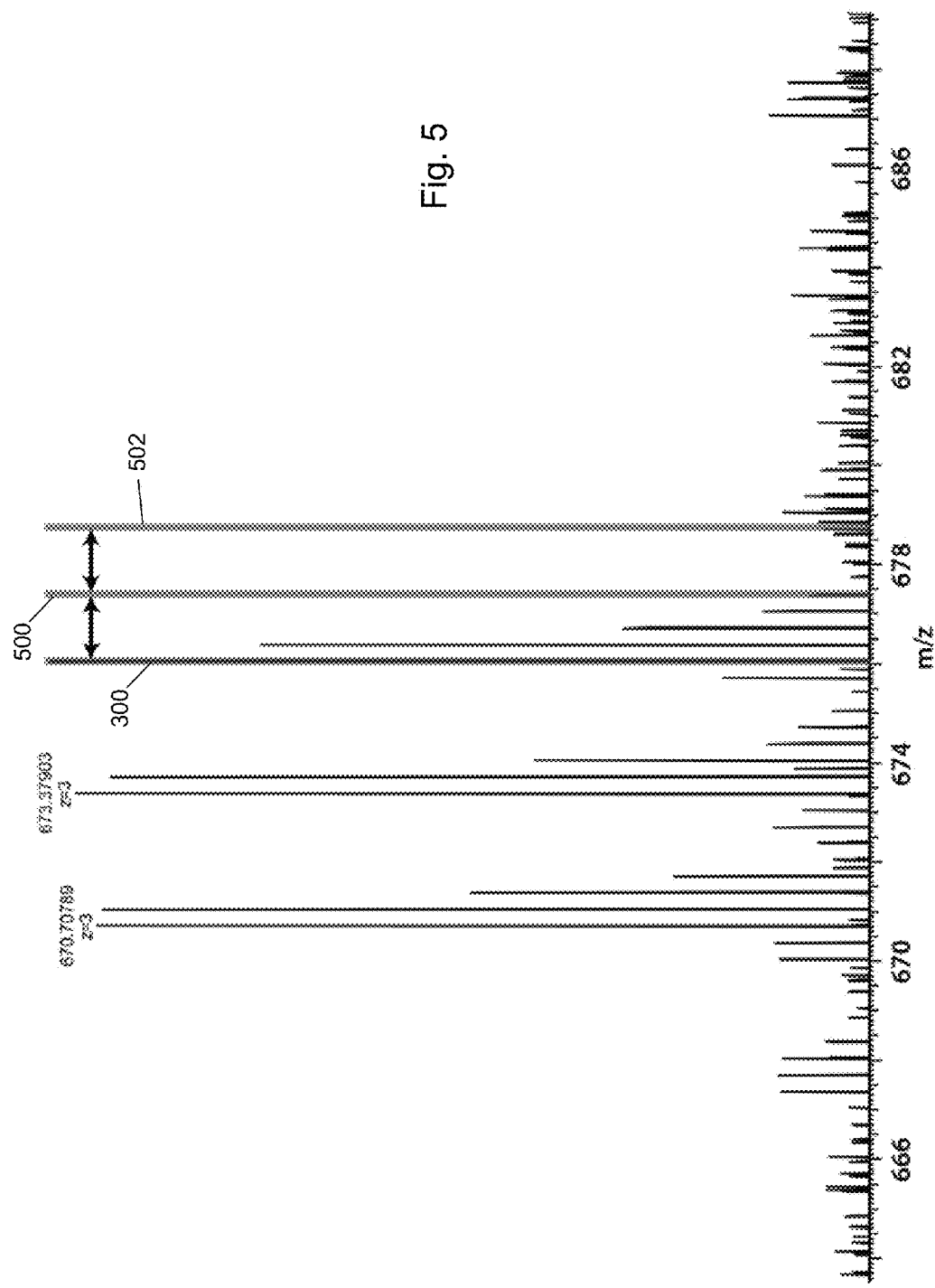
FIG. 5 depicts the MS1 mass spectrum plot of FIG. 4 including a first set of triplex data points in accordance with an illustrative embodiment.
Figure 6:
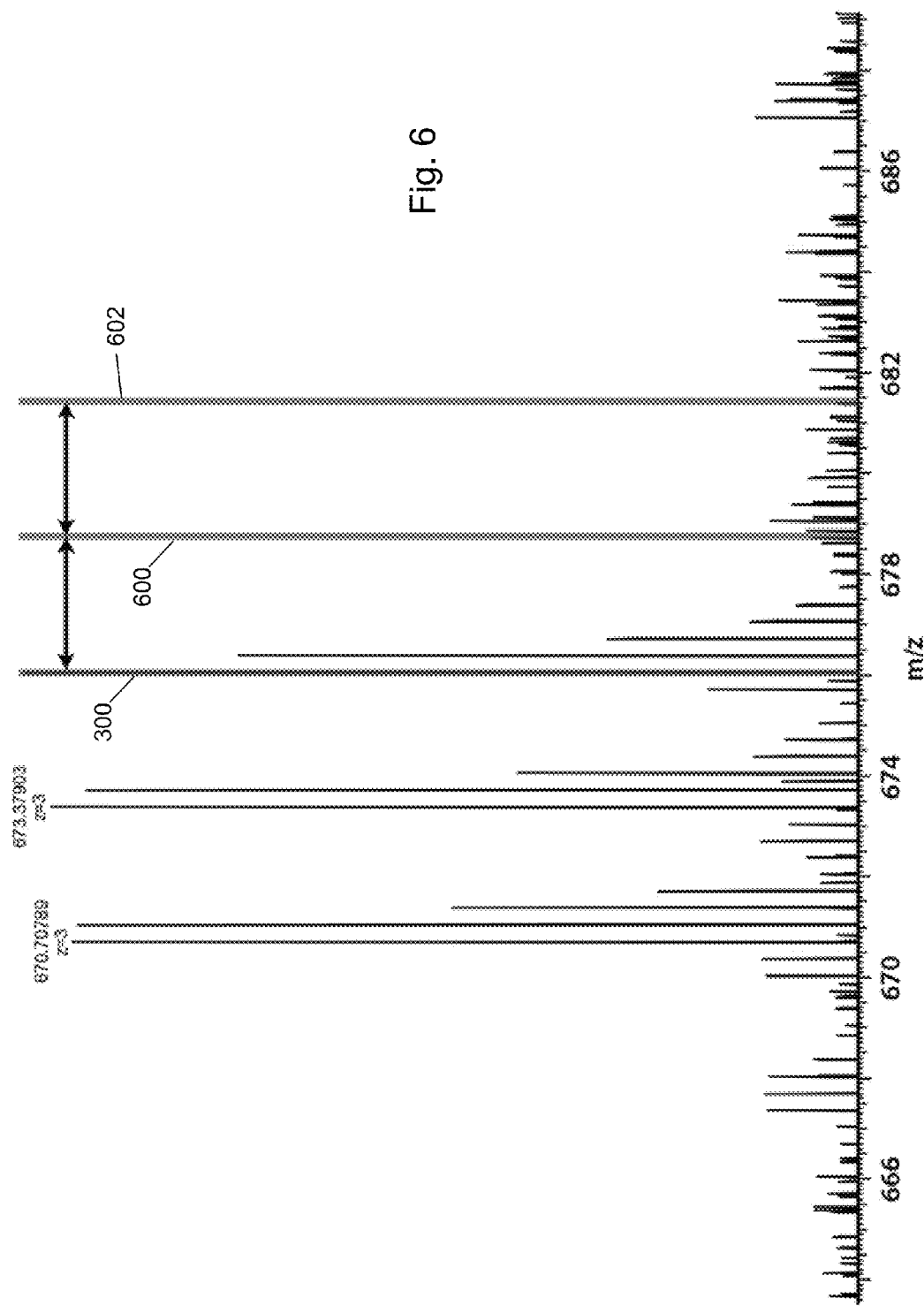
FIG. 6 depicts the zoomed MS1 mass spectrum plot of FIG. 4 including a second set of triplex data points in accordance with an illustrative embodiment.
Figure 7:
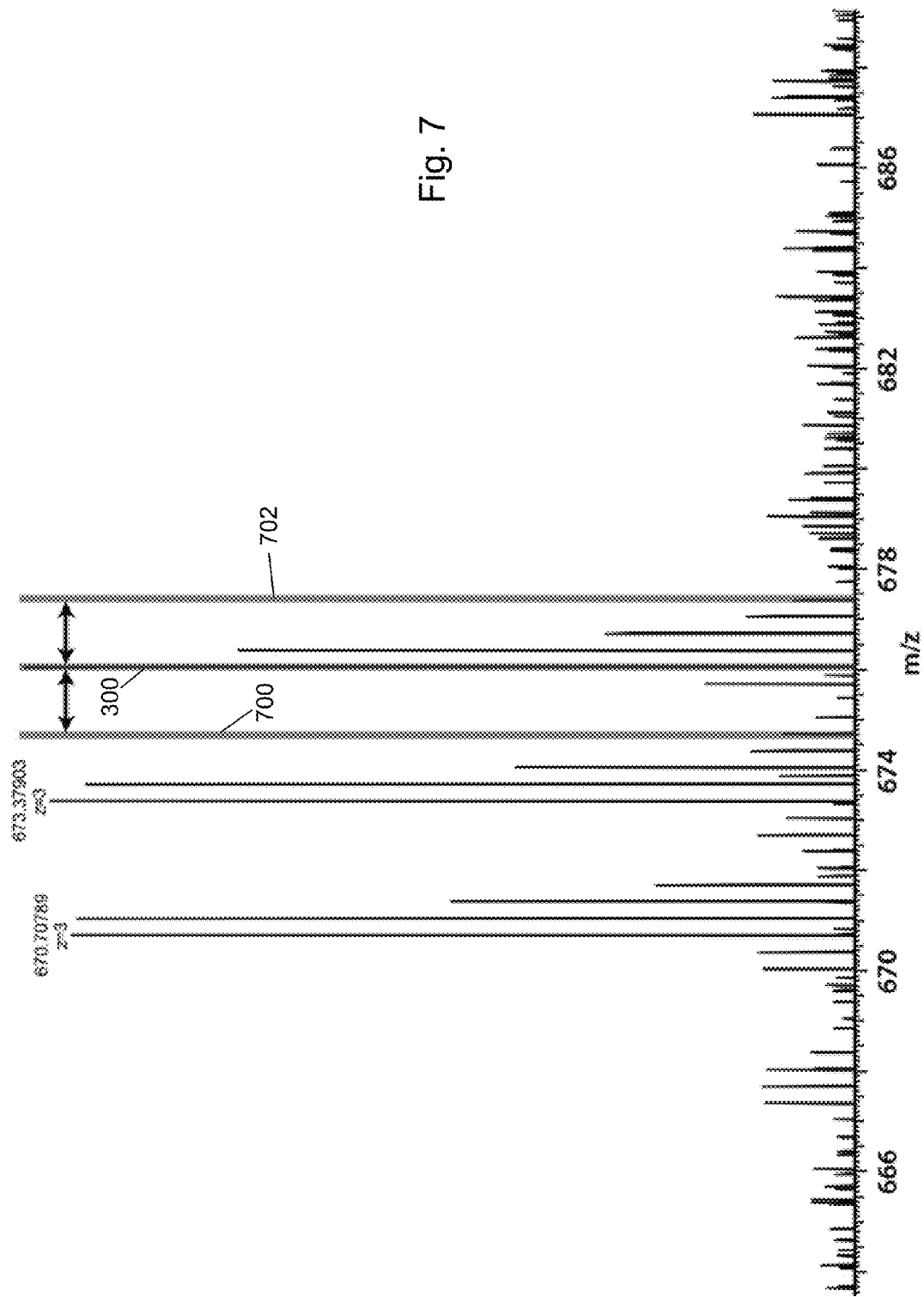
FIG. 7 depicts the zoomed MS1 mass spectrum plot of FIG. 4 including a third set of triplex data points in accordance with an illustrative embodiment.

For illustration, with reference to FIG. 5, a first peak location 500 and a second peak location 502 are identified based on the assumption that the selected peak is the light tag type, there is a single tag, and a known charge state of +3 resulting in a Δm/z=1.3357 for m=4.007 Da. With reference to FIG. 6, a first peak location 600 and a second peak location 602 are identified based on the assumption that the selected peak is the light tag type, there are two tags, and a known charge state of +3 resulting in a Δm/z=2.6714. With reference to FIG. 7, a first peak location 700 and a second peak location 702 are identified based on the assumption that the selected peak is the medium tag type, there is a single tag, and a known charge state of +3 resulting in a Δm/z=1.3357 subtracted from $(m/z)_{SP}$ to determine first peak location 700 and added to $(m/z)_{SP}$ to determine second peak location 702.

With continuing reference to FIG. 2, in an operation 208, an intensity value is determined from the MS1 spectra data at each of the possible related peak locations of the set of related peaks determined in operation 206. In an operation 210, an intensity score is calculated based on the intensity values as $$S = \sum_{i=1}^{N_S} \text{Log}(I_i(W))$$

where $N_S$ is the number of related peaks in the set of related peaks, $I_i$ is the intensity value for the associated related peak at a given width W. For example, in identifying an intensity value, an intensity peak value may be determined over a mass-to-charge ratio window having the width W selected based on the precision of tandem mass spectrometer 102. Of course, this value may be defined by the user or defined from characteristic data defined for tandem mass spectrometer 102.

The intensity value determined from the MS1 spectra data at each of the related peak locations may be compared to a threshold, $T_N$, before calculating the intensity score. If the intensity value is below the threshold, a value of zero may be added to the intensity score. The threshold, $T_N$, may be defined as a noise threshold of tandem mass spectrometer 102. Of course, this value also may be defined by the user or defined from characteristic data defined for tandem mass spectrometer 102.

In an operation 212, a determination is made concerning whether or not there is another tag variation to process. For example, tag variations may be associated with the possible values of $N_T$ and $N_C$. If there is another tag variation, for example, and an additional number of tags or an additional charge state to consider, processing continues in operation 206 to calculate additional possible peak locations relative to the selected peak. If all of the possible tag variations have been evaluated, processing continues in an operation 214.

In operation 214, a determination is made concerning whether or not there is another tag type assumption to process. For example, if the experiment includes light, medium, and heavy tag types, each tag type is processed as the assumed tag type for the selected peak. If there is another tag type to process, processing continues in operation 204 to assume the next tag type for the selected peak and to calculate additional possible peak locations relative to the selected peak based on this assumed tag type. If all of the possible tag types have been evaluated, processing continues in an operation 216.

The intensity score calculated for each set of peak locations may be stored in computer-readable medium 114 or in database 126. As an example, the intensity score may be stored as a table of values in association with the tag type assumed in operation 204 and for each tag variation assumed in operations 204/212. With reference to FIG. 8, a table 800 of intensity scores calculated for a plurality of sets of triplex data points is shown in accordance with an illustrative embodiment. In this illustrative embodiment, the experiment included light, heavy, and medium tag types and from one to five tags with a known charge state. The indicators light, heavy, and medium indicate the assumed tag type. Of course, if the charge state is not known, table 800 includes an additional dimension associated with the possible charge states.

With continuing reference to FIG. 2, in operation 216, a determination is made concerning whether or not a matching set of related peaks has been identified. For example, the entry in table 800 having the maximum score value may be selected as defining a matching set of related peaks. In an illustrative embodiment, the maximum score value may be compared to an overall threshold value, $T_O$, before selecting the maximum score value as a match. If the maximum score value is below the threshold value, $T_O$, no match may be identified. The threshold value, $T_O$, may be defined by the user as an input or defined based on a signal-to-noise ratio (S/N), an absolute number of counts, and/or mass accuracy of the peaks measured by tandem mass spectrometer 102. If no match is identified in operation 216, processing continue in an operation 220. If a match is identified in operation 216, processing continue in an operation 218. In operation 218, the matching set of peak data points is added to an MS2 queue for sequential MS2 processing by tandem mass spectrometer 102.

For illustration, a maximum score value 802 shown with reference to FIG. 8, may be selected as identifying a matching set of related peaks because it is the maximum score and exceeds the threshold, $T_O$. The matching set of related peaks was located with a number of tags value of two and assuming the selected peak was the heavy tag type. As a result, the location of the matching related peaks are identified at a first m/z value of $(m/z)_{SP}-\Delta m/z$ and at a second m/z value of $(m/z)_{SP}-2\times\Delta m/z$.

For illustration, with reference to FIG. 9, the matching triplex of data points is identified as a light peptide peak 900, a medium peptide peak 902, and a heavy peptide peak 904. Heavy peptide peak 904 corresponds to the selected peak 300. Execution of operations 204 to 218 correctly identified the set of related peaks visually identifiable as second peak 302, third peak 304, and first peak 300 in FIG. 4. Light peptide peak 900, medium peptide peak 902, and heavy peptide peak 904 are added to the MS2 queue for MS2 processing by tandem mass spectrometer 102 in operation 218. The selected peptide peaks may be sequentially isolated, fragmented, and the resulting fragment ion m/z values recorded, producing MS2 spectra data. The identification and of one or more peptides in sample stream 106 may be determined using the MS2 spectra data. Further quantification is also possible if the peptides were labeled using a tagging/labeling method that also enables quantification from MS2 spectra.

Figure 10A:
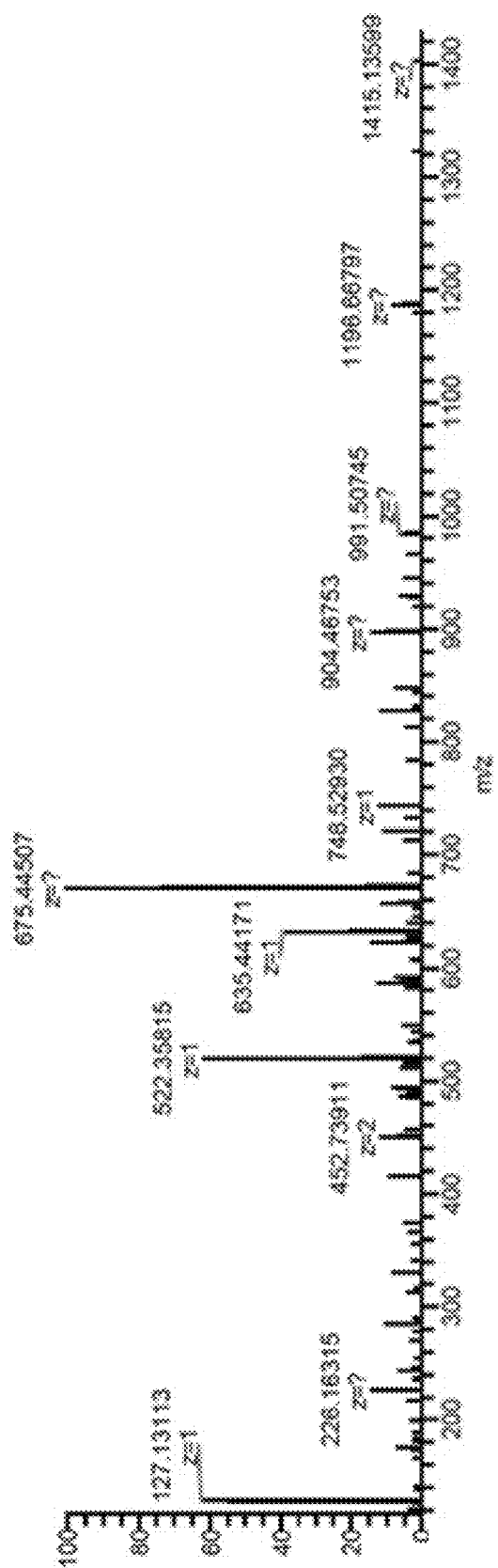
FIG. 10a depicts an MS2 mass spectrum plot for a first data point of the matching triplex of FIG. 9 in accordance with an illustrative embodiment.
Figure 10B:
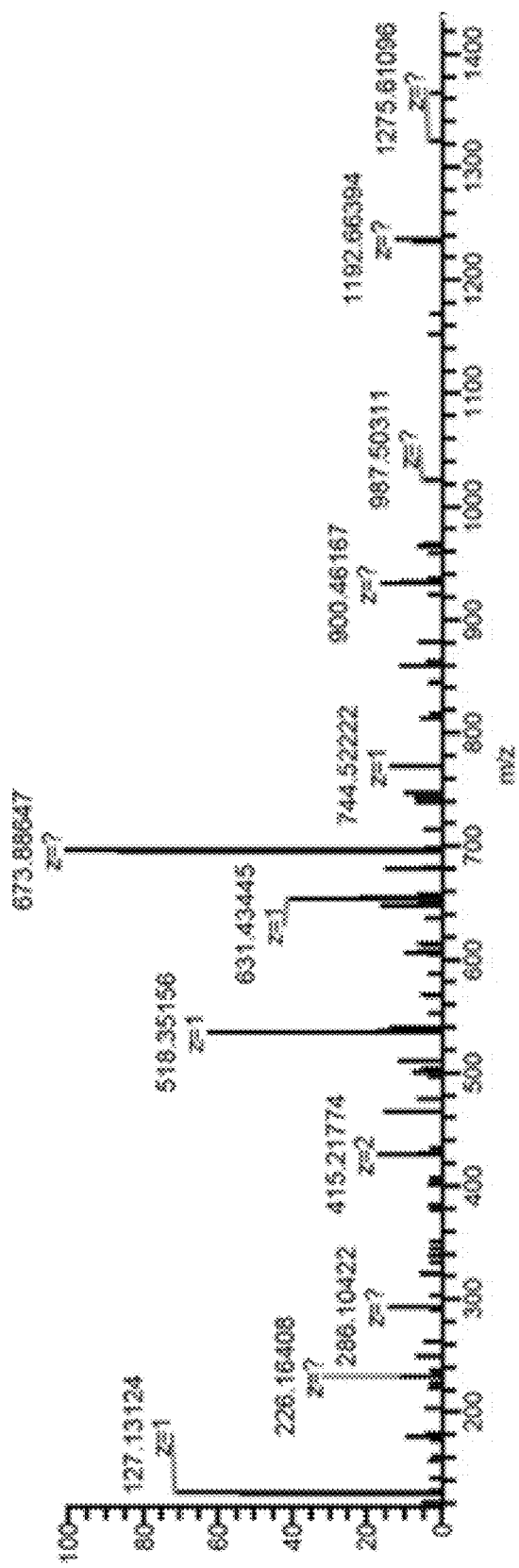
FIG. 10b depicts an MS2 mass spectrum plot for a second data point of the matching triplex of FIG. 9 in accordance with an illustrative embodiment.
Figure 10C:
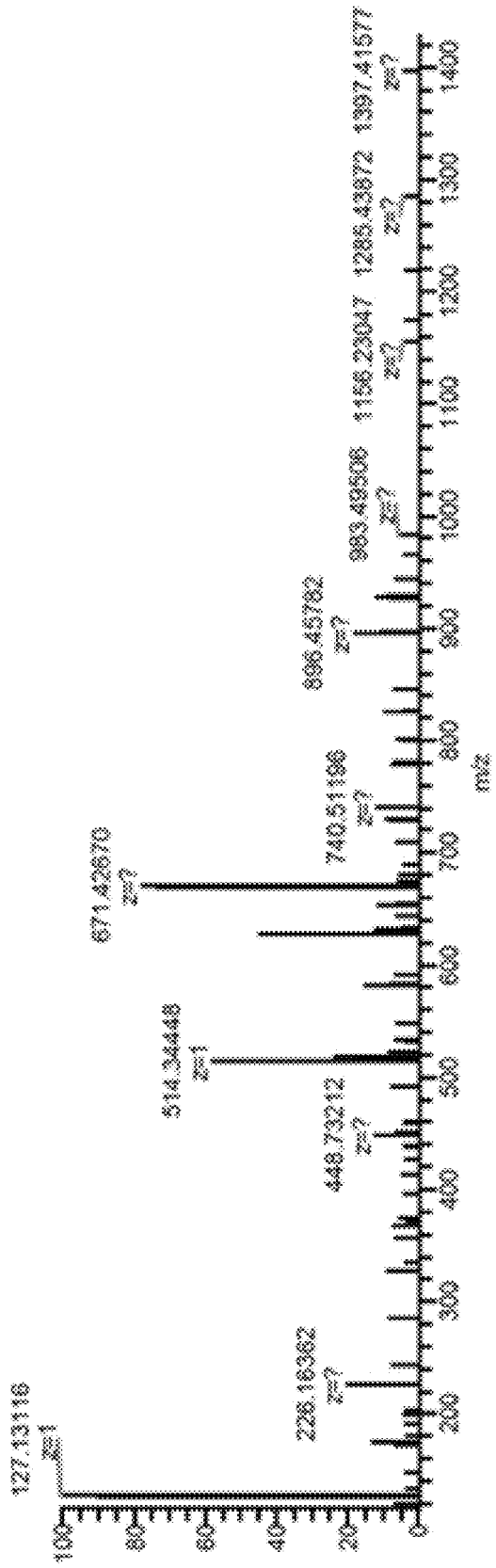
FIG. 10c depicts an MS2 mass spectrum plot for a third data point of the matching triplex of FIG. 9 in accordance with an illustrative embodiment.

With reference to FIG. 10a, an MS2 mass spectrum plot for heavy peptide peak 904 is shown in accordance with an illustrative embodiment. With reference to FIG. 10b, an MS2 mass spectrum plot for medium peptide peak 902 is shown in accordance with an illustrative embodiment. With reference to FIG. 10c, an MS2 mass spectrum plot for light peptide peak 900 is shown in accordance with an illustrative embodiment. Because of the sequential processing of the set of related peaks, the related peptides were processed closely spaced in time (e.g., within one second of each other), which improves the consistency and repeatability of the experiment and ensures minimal deviation in quantitative accuracy (i.e., minimizing the difference of interfering peptides and/or changing chemical background). For example, the MS1 background ions that cause loss of quantitative accuracy during isobaric tagging change within seconds as contaminants come and go. If the partner peaks are sampled at large time intervals (e.g., 5 seconds, 10 seconds, 20 seconds or more), the quantitative accuracy is degraded.

With continuing reference to FIG. 2, in an operation 220, a determination is made concerning whether or not another peak is selected for processing. For example, a user may make a selection initially to define the number of peaks processed. A simple counter or other methods known to those skilled in the art may be used to determine if all of the peaks have been processed. If another peak is to be processed, processing continues at operation 202 to select another peak and determine if the selected peak has any related peaks for sequential processing. If another peak is not to be processed, processing may stop or may continue at another time as part of an on-going experiment. The MS2 processing may continue as long as there are peaks in the MS2 queue or until stopped by the user. The identification of one or more peptides in sample stream 106 may be determined using the MS2 spectra data.

In an alternative embodiment, instead of adding the matching set of related peaks to the MS2 queue for MS2 processing by tandem mass spectrometer 102, the matching set of related peaks may be deliberately excluded from the MS2 queue for MS2 processing by tandem mass spectrometer 102. For example, in SILAC labeling experiments, proteomic sampling depth may be improved by not selecting the SILAC partners for MS2 sampling. Since all of the quantitative information is contained within the MS1 spectrum, oversampling of the same precursor does not improve data quality and reduces duty cycle, which may lower the sampling depth. In an illustrative embodiment, in a SILAC labeling experiment the decision may be made to perform MS2 sampling of only a predefined one of the matching set of related peaks. For example, only the light peptide version may be selected for MS2 processing. Of course, alternatively, only the heavy peptide version may be selected for MS2 processing.

Selecting the wrong set of related peaks wastes time due to the additional MS2 processing of each related peak and may generate incomplete data (i.e., only two of the three related peaks were correctly identified). Selecting the wrong set of related peaks is more likely to occur when there is a large dynamic range between the MS1 intensities of a set of related peaks such that a precursor has a low S/N. Triggering a selected ion monitoring (SIM) scan around the set of related peaks and reanalyzing the data increase the S/N of the precursors due to gas-phase enrichment, which improves the likelihood of correctly locating the related peaks. To reduce the impact of additional analyses on the overall duty cycle, the additional scan may be triggered on only related peaks that are difficult to identify.

Interfering peaks may skew the assignment of related peaks. For example, an intense, nearby peak may result in identifying a related peak cluster that doesn't actually exist. True related peak clusters have nearly identical profiles, because they are isochemic and elute together, while non-isochemic interferences likely have a different elution profile. Thus, by comparing the elution profiles of the m/z over time, the difference can be evaluated and used as a filter to improve the identification of true related peak clusters. Because true related peak clusters are isochemic, their relative isotopic ratios should be identical as well regardless of their absolute intensity. Thus, by comparing the isotopic ratios of the peaks to check for similarities, interfering species can be identified and filtered out using this comparison as well.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:
1. A device comprising:
    a processor; and
    a computer-readable medium operably coupled to the processor, the computer-readable medium having computer-readable instructions stored thereon that, when executed by the processor, cause the device to
        select an intensity peak from MS1 spectra data generated for a sample by a tandem mass spectrometer;
        identify a peak location for the selected intensity peak;
        calculate an intensity score, from the MS1 spectra data, for each of a plurality of possible related peak locations based on an intensity value associated with each of the plurality of possible related peak locations;
        determine if any of the plurality of possible related peak locations forms a related peak set based on the calculated intensity score for each of the plurality of possible related peak locations, wherein the related peak set includes the identified peak location; and
        when a related peak set is formed, perform an MS2 scan for at least one peak location selected from the related peak set using the tandem mass spectrometer.
2. The device of claim 1, further comprising the tandem mass spectrometer.
3. A non-transitory computer-readable medium having stored thereon computer-readable instructions that, when executed by a computing device, cause the computing device to:
    select an intensity peak from MS1 spectra data generated for a sample by a tandem mass spectrometer;
    identify a peak location for the selected intensity peak;
    calculate an intensity score, from the MS1 spectra data, for each of a plurality of possible related peak locations based on an intensity value associated with each of the plurality of possible related peak locations;
    determine if any of the plurality of possible related peak locations forms a related peak set based on the calculated intensity score for each of the plurality of possible related peak locations, wherein the related peak set includes the identified peak location; and
    when a related peak set is formed, perform an MS2 scan for at least one peak location selected from the related peak set using the tandem mass spectrometer.
4. The non-transitory computer-readable medium of claim 3, wherein the sample is generated as a sample stream from a liquid chromatography column.
5. The non-transitory computer-readable medium of claim 3, wherein the MS1 spectra data is generated by a survey scan that determines a mass-to-charge ratio of intact peptides.
6. The non-transitory computer-readable medium of claim 3, wherein the computer-readable instructions further cause the computing device to select all of the peak locations in the related peak set to perform the MS2 scan for each of the plurality of possible related peak locations determined to be a related peak in the related peak set.
7. The non-transitory computer-readable medium of claim 3, wherein the computer-readable instructions further cause the computing device to not perform the MS2 scan for each of the plurality of possible related peak locations determined to be a related peak in the related peak set.
8. The non-transitory computer-readable medium of claim 3, wherein a possible related peak location is determined based on

$$\Delta m/z = \frac{N_T \times m}{N_C},$$

where $N_T$ is a number of tags, m is a mass defined based on a chemical tag type, and $N_C$ is a charge state number.
9. The non-transitory computer-readable medium of claim 8, wherein the charge state number is known and treated as a constant for each of the plurality of possible related peak locations.
10. The non-transitory computer-readable medium of claim 8, wherein the number of tags is defined as a range of values and the plurality of possible related peak locations are defined by iterations through the range of values.
11. The non-transitory computer-readable medium of claim 3, wherein the intensity score is calculated for a set of related peaks using $S=\Sigma_{i=1}^{N_S} \text{Log}(I_i(W))$, where S is the intensity score, $N_S$ is a number of possible peaks in the set of related peaks, $I_i$ is the intensity value for the associated related peak of the plurality of possible related peak locations at a given width W.
12. The non-transitory computer-readable medium of claim 11, wherein the set of related peaks is associated with a plurality of tag types.
13. The non-transitory computer-readable medium of claim 12, wherein the possible related peak locations are determined based on an assumption that the selected peak is one of the plurality of tag types.
14. The non-transitory computer-readable medium of claim 11, wherein the intensity score is calculated for the set of related peaks only if the intensity value for each related peak of the set of related peaks satisfies a threshold value.
15. The non-transitory computer-readable medium of claim 3, wherein the related peak set is determined as the selected intensity peak and the possible related peak location that results in a maximum value of the calculated intensity score.
16. The non-transitory computer-readable medium of claim 15, wherein the related peak set is determined only if the calculated intensity score satisfies a threshold value.
17. The non-transitory computer-readable medium of claim 3, wherein the computer-readable instructions further cause the computing device to select a second intensity peak from the MS1 spectra data generated for the sample by the tandem mass spectrometer.
18. The non-transitory computer-readable medium of claim 3, wherein calculating the intensity score comprises:
    identifying a possible related peak location based on a calculated differential location value and the identified peak location for a set of related peaks;
    determining an intensity value associated with the identified possible related peak location from the MS1 spectra data; and
    adding the determined intensity values for each possible related peak location of the set of related peaks.
19. The non-transitory computer-readable medium of claim 18, wherein the set of related peaks is associated with a plurality of tag types.
20. A method of identifying a related peak set from MS1 spectra data, the method comprising:
    selecting, by a processor, an intensity peak from MS1 spectra data generated for a sample by a tandem mass spectrometer;
    identifying, by the processor, a peak location for the selected intensity peak;

calculating, by the processor, an intensity score, from the MS1 spectra data, for each of a plurality of possible related peak locations based on an intensity value associated with each of the plurality of possible related peak locations; and determining, by the processor, if any of the plurality of possible related peak locations forms a related peak set based on the calculated intensity score for each of the plurality of possible related peak locations, where in the related peak set includes the identified peak location; and when a related peak set is formed, performing an MS2 scan by the tandem mass spectrometer for at least one peak location selected from the related peak set.

* * * * *